United States Patent [19]

Wasley

[11] Patent Number: 5,015,645
[45] Date of Patent: May 14, 1991

[54] TETRACYCLIC PYRROLE LACTAM DERIVATIVES

[75] Inventor: Jan W. F. Wasley, Chatham, N.J.

[73] Assignee: Ciba-Geigy Corporation, Ardsley, N.Y.

[21] Appl. No.: 424,014

[22] Filed: Oct. 19, 1989

[51] Int. Cl.$^5$ .................. C07D 487/18; C07D 487/10; A61K 31/55; A61K 31/495

[52] U.S. Cl. ................... 514/250; 540/556; 544/343; 544/231; 546/183; 548/526; 548/561; 560/126; 562/508

[58] Field of Search ...................... 544/343; 514/250

[56] References Cited

U.S. PATENT DOCUMENTS 4,897,399  1/1990  Wasley .................... 514/288

OTHER PUBLICATIONS

Martin et al., Tetrahedron Letters, 1979, 3823-3826.
Martin et al., J. Am. Chem. Soc., 102, 5274-5279 (1980).
Tsuda et al., Heterocycles, 15, 431-436 (1981).
Hajicek, Chem. Abstract, 103, 104946x (1985).
Takevosyan, Chem. Abstract, 72, 121395c (1970).
Isobe, Chem. Abstract, 108, 150777w (1988).
Isobe, Chem. Abstract, 108, 167746h (1988).
Mondon et al., Chem. Ber., 92, 2552 (1959).

*Primary Examiner*—Mark L. Berch
*Attorney, Agent, or Firm*—Norbert Gruenfeld

[57] ABSTRACT

Disclosed are the compounds of formula I

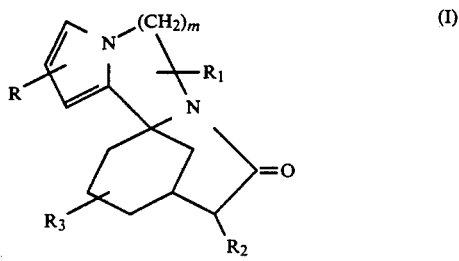

wherein R and $R_1$-$R_3$ independently represent hydrogen or lower alkyl, and m represents the integer 2 or 3; their methods of preparation; pharmaceutical compositions thereof, and their use for treating cognitive disorders in mammals.

7 Claims, No Drawings

TETRACYCLIC PYRROLE LACTAM DERIVATIVES

SUMMARY OF THE INVENTION

The invention relates to the optionally substituted tetracyclic compounds of the general formula I as defined herein, which are useful in the prevention and treatment of cognitive dysfunction in mammals, processes for preparing same, pharmaceutical compositions comprising said compounds, and methods of treating conditions and syndromes in mammals responsive to improvement of cognitive performance by administration of said compounds to mammals in need thereof.

The compounds of this invention improve cognitive performance including memory and learning in mammals and can be used for the treatment of cognitive impairment, e.g. impairment of memory and learning, in mammals which occurs e.g. in conditions of amnesia, dementia (such as Alzheimer's disease or senile dementia), dyslexia, transient cerebral ischemia and the like.

DETAILED DESCRIPTION OF THE INVENTION

Particularly the invention is directed to the compounds of formula I

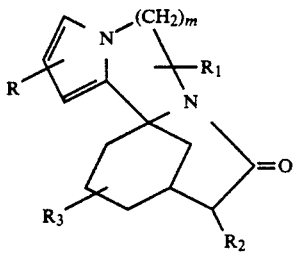

wherein R and $R_1$-$R_3$ independently represent hydrogen or lower alkyl, and m represents the integer 2 or 3.

In the compounds of the invention of formula I the ring junction between the cyclohexane and lactam rings may be either cis or trans fused. Furthermore, the compounds of the invention can also exist in the form of optically active isomers. The resulting racemic and optically active isomers are within the purview of the invention.

Preferred are said compounds of formula I wherein m represents the integer 2, as represented by formula II

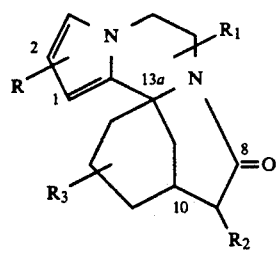

wherein R and $R_1$-$R_3$ independently represent hydrogen or lower alkyl.

Preferred in turn are said compounds of the formula II and particular embodiments thereof wherein the cyclohexane and piperidone rings are cis fused, as represented by formula III

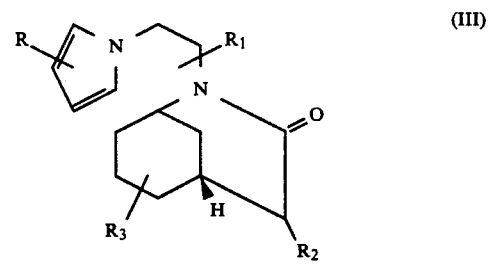

wherein R and $R_1$-$R_3$ represent hydrogen or lower alkyl.

A lower alkyl group within the scope of the invention may contain 1 to 7 carbon atoms, preferably 1 to 4 carbon atoms, and represents advantageously methyl.

The compounds of the invention are useful in mammals as nootropic agents for treating cerebral insufficiency, e.g. for improving memory and learning in conditions of cognitive dysfunction and are active in state of the art test systems indicative of such activity, e.g. as described in "Techniques and Basic Experiments for the Study of Brain and Behavior", Elsevier (Publisher), 1983.

The above-cited properties are demonstrable in tests using advantageously mammals, e.g. mice, rats, cats or monkeys. Said compounds can be applied in vivo either enterally or parenterally, advantageously orally, intraperitoneally or intravenously, e.g. within gelatin capsules, as aqueous suspensions or in aqueous solutions. The dosage may range between about 0.01 and 300 mg/kg, preferably between about 0.05 and 100 mg/Kg, advantageously between about 0.1 and 50 mg/Kg.

The above-cited properties can be determined, for instance, in the electroshock induced amnesia test in mice, e.g. described by Mondadori et al in Acta Neurol. Scand. 69, Suppl. 99, 125-129 (1984), in the step-down passive avoidance test in mice and rats, e.g. described by Mondadori in Psycholpharmacol. 63, 297-300 (1979) and Neuropharmacology 7, Suppl. 3, 27-38 (1986), and in the active avoidance test in aged rats.

The test to measure the inhibition of electroshock-induced amnesia in mice is carried out as follows:

The apparatus consists of a large box (35×20×10 cm) which is connected by means of a sliding door to a small box (10×10×18 cm). The small box is brightly lit from above by a 100 watt lamp, whereas the large box is dark. The floor of both compartments consists of an electrified grating, the rods of which (diameter: 6 mm) are each spaced 13 mm apart.

For treatment, male mice having a body weight of 20-22 g are placed into the brightly lit small box. As mice have an instinctive preference for the dark, they usually go into the dark compartment within 30 seconds. As soon as all the mice have entered this compartment, the sliding door is closed and a shock (1 mA, 5 seconds) is administered to the paws of the mice. The animals are then immediately taken out of the testing unit. Two separate assays are carried out (in the morning between 8 and 11 a.m. and in the afternoon between 12 noon and 3 p.m.)

To test their learning performance, the mice are once more placed individually into the lit compartment and the time until they are all in the dark (the step-through latency) is measured. Most of the animals will now normally remain in the lit compartment over the entire observation time of 150 seconds.

The memory of the shock applied to the paws is at least partially eliminated if an amnesia-inducing treatment, consisting of a brief electroshock treatment, is administered directly after the shock to the paws is applied in the training session. Parameters of the electroshock: 50 mA, 0.4 sec., 50 Hz.

To determine the protective action against the amnesia-inducing action of the electroshock, the animals are divided into different groups and the test compound is administered intraperitoneally 30 minutes before the training procedure, with vehicle alone (=placebo) being administered to control groups. The animals are subjected to electroshock treatment immediately after training. The degree of the learning performance still retained is measured 24 hours later from the residence time in the lit box (step-through latency period) compared with that obtained with control animals to which vehicle only has been administered.

Prolongation of the step-through latency period in the electroshock treated animals is indicative of enhancement of retention performance by the test compound.

Illustrative of the invention, the compound of example 1 prolongs the step-through latency in the electroshock-induced amnesia model (inhibits electroshock-induced amnesia) at a dose of e.g. about 3 mg/Kg i.p. in mice.

The step-down passive avoidance test to measure the enhancement of learning and memory (of retention performance) in mice is carried out as follows:

The apparatus consists of an electrified grid (50×50 cm) of stainless steel rods (4 mm in diameter, 13 mm distance between bars), enclosed by grey PVC walls 50 cm in height. In the middle of the grid is a wooden platform 12 mm high and 67 mm in diameter, which is enclosed by a removable grey PVC tube (18 cm high, 68 mm inner diameter).

Male mice (20–22g) are placed one by one on the platform inside the tube, which is removed after 10 seconds. With a few exceptions the mice step-down from the platform within 20 seconds to explore. As soon as the animal has all four feet on the grid, it receives a footshock (1 mA, 1 sec) and is then immediately removed from the apparatus. The latency period until the animal descends is measured (baseline latency).

Twenty-four hours after the training, each animal is again placed on the platform and the "step-down latency" is recorded (retest latency) up to a cut-off time of 150 sec. Any prolongation of the retest step-down latency in comparison to the baseline is rated as a sign of learning.

The test compounds are administered to groups of 25 mice for each dose 30 minutes (i.p.) or 60 minutes (p.o.) before the training session or immediately after the shock is applied. The degree of enhancement of learning and memory is assessed 24 hours later by measuring the step-down latency period. Any increase in the latency period compared to control is indicative of the enhancement in retention performance by the test compound.

Illustrative of the invention, the compound of example 1 significantly improves performance in the step-down passive avoidance test in mice at a dose of e.g. about 3 mg/Kg i.p. administered 30 minutes prior to the training session.

The effect on age-related cognitive dysfunction is determined in aged rats as follows:

Groups of rats (age 27 months at the beginning of the experiment) are treated daily p.o. with various doses of test compound or vehicle. Sixty minutes later they are subjected to a learning session in a one-way active avoidance task. A second learning session is repeated about 4 hours later.

The apparatus consists of two identical compartments measuring 20×20×30 cm with electified grid floors and a connecting door (12×16 cm).

The training session consists in placing an animal into compartment A. After a delay of 10 seconds a foot-shock current is turned on. By moving into compartment B the animals can either escape or avoid the footshock. Active avoidance training is continued until the animals meet the criterion of 5 consecutive avoidances. A reduction in the number of training sessions required is indicative of a facilitation in learning the active avoidance task.

The aforementioned advantageous properties render the compounds of the invention useful for improving cognitive performance and for the treatment cognitive dysfunction in mammals including man, particularly for the treatment of conditions of impaired memory and learning, e.g. in senile dementia, Alzheimer's disease and dyslexia.

The compounds of the invention are prepared by processes comprising:

(a) cyclizing a compound of the formula

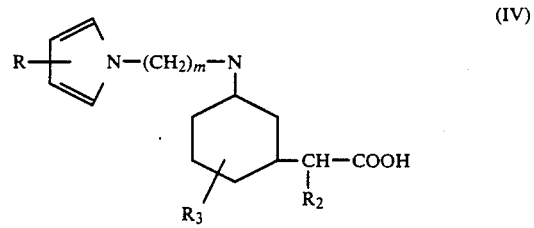

or a reactive ester derivative thereof wherein m, R, $R_2$ and $R_3$ have meaning as defined above and the chain $(CH_2)_m$ is optionally substituted by lower alkyl; or (b) cyclizing a compound of the formula

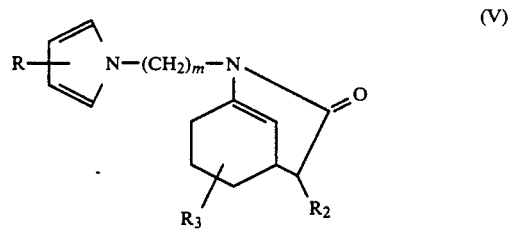

wherein m, R, $R_2$ and $R_3$ have meaning as defined hereinabove; and the chain $(CH_2)_m$ is optionally substituted by lower (c) cyclizing a compound of the formula

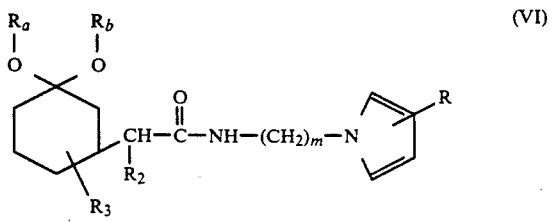

wherein $R_a$ and $R_b$ represent lower alkyl or a combined represent lower alkylene; R, $R_2$, $R_3$, and m have meaning as defined hereinabove, and the $(CH_2)_m$ chain is optionally substituted by lower alkyl, by treatment with an (d) condensing a compound of the formula

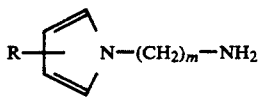

(VII)

wherein R and m have meaning as defined hereinabove, and wherein the $(CH_2)_m$ chain is optionally substituted by lower alkyl, with a compound of the formula

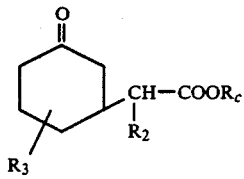

(VIII)

wherein $R_2$ and $R_3$ have meaning as defined hereinabove, $R_c$ represents hydrogen or lower alkyl; and treating the resulting product in situ with an anhydrous acid; or (e) reducing the ketone functional group in a compound of the formula

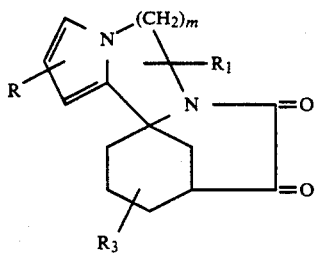

(IX)

wherein m, R, $R_1$ and $R_3$ have meaning as defined hereinabove; or (f) hydrolyzing and/or decarboxylating a compound of the formula

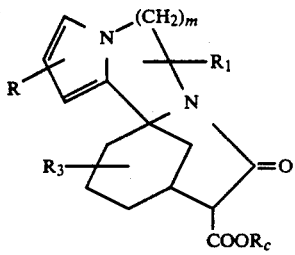

(X)

wherein R, $R_1$, and $R_3$ and m have meaning as defined hereinabove, and $R_c$ represents hydrogen or lower alkyl.

In the above cited processes, the said process is carried out while, if necessary, temporarily protecting any interfering reactive group(s), and then liberating the resulting compound of the invention; and, if required or desired, a resulting compound of the invention is converted into another compound of the invention, and/or, if desired, a resulting free compound is converted into a salt or a resulting salt is converted into the free compound or into another salt; and/or a mixture of isomers or racemates obtained is separated into the single isomers or racemates; and/or, if desired, a racemate is resolved into the optical antipodes.

In structural formulae herein, dotted lines in addition to a single bond indicate that a double bond is located between any two adjacent atoms between which dotted lines are indicated.

In starting compounds and intermediates which are converted to the compounds of the invention in a manner described herein, functional groups present, such as carboxy, amino (including ring NH) and hydroxy groups, are optionally protected by conventional protecting groups that are common in preparative organic chemistry. Protected carboxy, amino and hydroxy groups are those that can be converted under mild conditions into free carboxy, amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxy, hydroxy group, amino group, etc.), the structure and stability of the molecule of which the substituent is a part and the reaction conditions.

Well-known protecting groups that meet these conditions and their introduction and removal are described, for example, in J.F.W. McOmie, "Protective Groups in Organic Chemistry", Plenum Press, London, N.Y., 1973, T.W. Greene, "Protective Groups in Organic Synthesis", Wiley, N.Y., 1984.

As referred to in the context of the application reactive ester derivatives of carboxylic acids include those generally known in the art, particularly lower alkyl esters and cyanomethyl esters.

A reactive esterified hydroxy group as mentioned herein represents a leaving group, particularly hydroxy esterified by a strong acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example methanesulfonyloxy, phenylsulfonyloxy or 4-methylphenylsulfonyloxy (tosyloxy).

The cyclization under process (a) is carried out optionally in the presence of an anhydrous acid such as glacial acetic acid or polyphosphoric acid in an inert solvent such as ethanol, toluene or xylene, preferably at an elevated temperature ranging from about 60° to 175°.

The starting materials of formula IV are prepared preferably in situ, e.g. by condensation of a compound of formula VII as defined above with a compound of formula VIII as defined above, preferably wherein $R_c$ represents lower alkyl, in an inert solvent, such as toluene, with simultaneous removal of water.

The cyclization according to process (b) is carried out essentially as described under process (a).

The starting materials of formula V can be preferably prepared in situ by heating e.g. a lower alkyl ester of a compound of formula IV in an inert solvent such as toluene.

The starting materials of formula V can also be prepared by condensing a compound of the formula XI

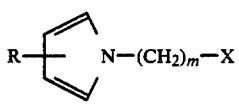

wherein R and m have meaning as defined hereinabove, the $(CH_2)_m$ chain is optionally substituted by lower alkyl and X represents reactive esterified hydroxy, such as halo, with a compound of the formula XII

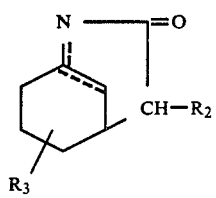

wherein $R_2$ and $R_3$ have meaning as defined hereinabove.

The starting materials of formula XII can be prepared in situ by e.g. condensing an ester of formula VIII above with ammonia or a salt thereof and removing the water generated during the condensation e.g. by azeotropic distillation.

The cyclization according to process (c) can be carried out by treatment of a compound of formula VI with an acid, e.g. phosphoric acid or polyphosphoric acid in toluene at elevated temperature.

The starting materials of formula VI can in turn be prepared by condensation of e.g. an acid of formula XIII

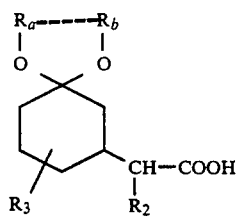

wherein $R_a$ and $R_b$ represent lower alkyl or $R_a$ and $R_b$ combined represent lower alkylene; $R_2$ and $R_3$ have meaning as defined above, with an amine of formula VII above, e.g. in the presence of a condensing agent such as dicyclohexylcarbodiimide.

The one step condensation according to process (d) is carried out e.g. in an inert solvent such as toluene or xylene with removal of water at or near reflux temperature, or in the presence of an acid such as acetic acid in an inert solvent such as ethanol or toluene.

The starting materials of formula VII and VIII can be prepared according to methods known in the art.

The reduction according to process (e) can be carried out according to procedures known in the art for selectively converting a ketone carbonyl grouping to the corresponding $CH_2$ grouping, e.g. under conditions of a Wolff-Kishner reaction.

The starting materials of formula IX can be prepared, e.g. by first condensing a compound of formula VII wherein m represents the integer 2 with a compound of formula VIII wherein $R_c$ represents lower alkyl, under conditions described in process (d) to obtain a compound of formula XIV which is condensed with oxalyl chloride to obtain a compound of formula XV

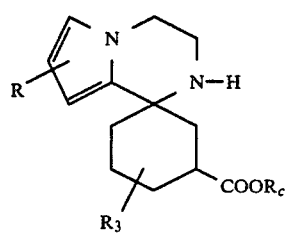

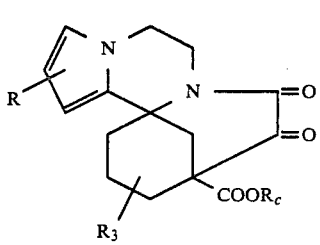

wherein R and $R_3$ have meaning as defined hereinabove and $R_c$ is lower alkyl. Conversion to the decarboxylated product of formula IX can be carried out e.g. by treatment with magnesium chloride in dimethylsulfoxide.

The conversion to the decarboxylated product according to process (f) can be carried out, e.g. by treatment of a compound of formula X with e.g. magnesium chloride in dimethyl sulfoxide or other methods known for the decarboxylation of similarly substituted $\beta$-keto esters.

The starting materials of formula X can be prepared by according to process (d) condensing a compound of formula VII above with a compound of formula VIII hereinabove, wherein $R_3$ has meaning as defined, but wherein $R_2$ represents COORc in which Rc represents lower alkyl.

The starting materials of formula X also possess biological properties similar to those described for the compounds of formula I-III and are therefore also useful for treating cerebral insufficiency in mammals, e.g. for improving memory and learning in conditions of cognitive dysfunction, as described herein for compounds of formula I.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Advantageously those starting materials are used in said reactions that lead to the formation of those compounds indicated above as being preferred.

The invention also relates to any novel starting materials and processes for their manufacture.

Depending on the choice of starting materials and methods, the new compounds may be in the form of one of the possible isomers or mixtures thereof, for example, depending on the number of asymmetrical carbon atoms, as pure optical isomers, as racemates or as mixtures of diastereomeric racemates including cis and trans ring fused isomers. The aforesaid possible isomers or mixtures thereof are within the purview of this invention.

Any mixtures of isomers can be separated on the basis of the physico-chemical differences of the constituents, in known manner, into the pure isomers for example by chromatography and/or fractional crystallization.

Resulting racemates can be resolved into the optical antipodes by known methods, including chiral chromatography. Racemic acid intermediates (those containing a carboxy group) can be resolved into their optical antipodes, e.g., by the fractional crystallization of d- or l-(alpha-methylbenzylamine, cinchonidine, cinchonine, quinine, quinidine, ephedrine, dehydroabietylamine, brucine or strychnine)-salts. Advantageously, the more active of the two antipodes is isolated.

In view of the close relationship between free carboxylic acids and their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, e.g. for the treatment of disorders involving cognitive dysfunction, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders e.g. magnesium aluminum silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

The invention also relates to a method of improving cognitive performance and of treating cognitive disorders (conditions of cognitive dysfunction) in mammals, particularly conditions of impaired memory and learning, such as senile dementia and Alzheimer's disease, comprising the administration to a mammal in need thereof of an effective cognition (learning and memory) enhancing amount of a compound of the invention, preferably in the form of above-cited pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 20 and 200 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR).

Example 1

A solution of 1.3 g of 2-(1-pyrrolyl)-ethylamine, 2.0 g of methyl 3-oxocyclohexylacetate in 150 ml toluene is stirred and refluxed overnight using a Dean Stark water separator. The reaction is cooled and 7 ml glacial acetic acid is added. The solution is stirred and refluxed as before for 6 hours, cooled and the organic solvents are evaporated under reduced pressure. The residue is dissolved in ether and washed with ice cold 1N aqueous sodium hydroxide. The organic layer is separated, dried over magnesium sulfate, and filtered. The ether solution is evaporated under reduced pressure and the residue is crystallized from ether to give 5,6,10,11,12,13-hexahydro-10,13a-methano-13aH-pyrrolo[2',1':3,4]pyrazino[1,2-a]azocin-8(9H)-one, m.p. 130°–132°, the compound of formula II wherein R, $R_1$, $R_2$ and $R_3$ represent hydrogen.

The starting material, 2-(1-pyrrolyl)-ethylamine, is prepared as follows:

A solution of 140 g of ethylenediamine and 300 g of 2,5-dimethoxytetrahydrofuran in 2000 ml of dioxane and 1700 ml of glacial acetic acid is stirred and refluxed for 6 hours. The reaction mixture is then cooled and the solvents evaporated under reduced pressure at 60°. The dark residue is taken up in methylene chloride and ice and basified with 3N aqueous sodium hydroxide. The organic layer is separated and extracted into 5N aqueous hydrochloric acid. The acid extract is made basic with cooling and is extracted with methylene chloride. The organic phase is dried over magnesium sulfate, treated with 10 g of charcoal and filtered. The methylene chloride is evaporated under reduced pressure to give an N-acetyl-2-(1-pyrrolyl)-ethylamine as an oil.

A mixture of 220 g of N-acetyl-2-(1-pyrrolyl)-ethylamine as obtained above and 1800 ml of 10% aqueous sodium hydroxide is heated under reflux for 16 hours, cooled and then extracted with 2500 ml of methylene chloride. The organic layer is separated, dried over magnesium sulfate, treated with 20 g of charcoal and filtered. The filtrate is evaporated under reduced pressure to give an oil which is distilled under high vacuum at 0.2 mm Hg to give 2-(1- pyrrolyl)-ethylamine as a clear oil.

The other starting material, methyl 3-oxocyclohexylacetate is prepared as follows:

A solution of 30 ml of 2-cyclohexen-1-one in 35 ml anhydrous ethanol is added dropwise at a temperature below −10° to a reagent prepared from 0.1 g sodium, 100 ml of absolute ethanol and 50 ml of diethyl malonate. The reaction mixture is allowed to warm slowly and is stirred at room temperature overnight. The mixture is evaporated to dryness, the residue is dissolved in ether, the ether solution is washed with brine, dried, filtered and evaporated to dryness. The residue is distilled under reduced pressure to yield diethyl 3-oxocyclohexylmalonate, b.p. 147°/0.5 mm.

The diester (50 g) is treated with a mixture of 28 g of potassium hydroxide in 50 ml of water and stirred at room temperature overnight. Concentrated hydrochloric acid (75 ml) is added and the mixture is heated under reflux for 6 hours. Water (150 ml) is added and the solution is extracted with methylene chloride. The extract is dried and evaporated to dryness to yield 3-oxocyclohexylacetic acid.

A solution of 8 g of the above acid in 30 ml dichloromethane is treated with excess diazomethane to yield, after distillation of the product under high vacuum, methyl 3-oxocyclohexylacetate.

Example 2

Similarly prepared according to procedure given in Example 1 is the compound of formula I wherein R, $R_1$, $R_2$ and $R_3$ represent hydrogen, m represents the integer 3, starting from 1,3-diaminopropane so as to obtain 3-(1-pyrrolyl)-propylamine which is then condensed with methyl 3-oxocyclohexylacetate.

Example 3

A solution of 4.4 g of 2-(1-pyrrolyl)-ethylamine, 7.4 g of diethyl 3-oxocyclohexylmalonate (see example 1) in 170 ml of toluene is stirred and refluxed for 2 days using a Dean Stark water separator. The reaction is cooled and 7 ml glacial acetic acid is added. The solution is stirred and refluxed as before for 6 hours, cooled and the organic solvents are evaporated under reduced pressure. The residue is dissolved in ether and the solution is washed with ice cold 1N aqueous sodium hydroxide. The organic layer is separated, washed with dilute HCl, dried over magnesium sulfate, and filtered. The ether solution is evaporated under reduced pressure and the residue is crystallized from ether-hexane to give ethyl 5,6,8,9,10,11,12,13-octahydro-8-oxo-10,13a-methano-13aH-pyrrolo[2',1':3,4-pyrazino[1,2-a]-azocine-9-carboxylate m.p. 92°–94°, the compound of formula X wherein R, $R_1$ and $R_3$ represent hydrogen, Rc represents ethyl, and m is 2.

Example 4

A mixture of 2.75 g of 2-(1-pyrrolyl)-ethylamine, 5.1 g of methyl 3-oxocyclohexylacetate, 4 ml of glacial acetic acid and 50 ml of ethanol is heated under reflux overnight. The reaction mixture is evaporated to dryness and the residue is neutralized with 10% ammonium hydroxide solution. The mixture is extracted with methylene chloride, the extract is washed with saturated sodium bicarbonate solution and evaporated to dryness. The residue is purified by thin layer chromatography to yield the compound of example 1.

Example 5

(a) Preparation of 1,000 capsules each containing 25 mg of the active ingredient:

| Formula: | |
| --- | --- |
| 5,6,10,11,12,13-Hexahydro-10,13a-methano-13aH-pyrrolo[2',1':3,4]-pyrazino[1,2-a]azocin-8-(9H)-one | 25.0 g |
| Lactose | 192.0 g |
| Modified starch | 80.0 g |
| Magnesium stearate | 3.0 g |

Procedure

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

What is claimed is:

1. A compound of the formula

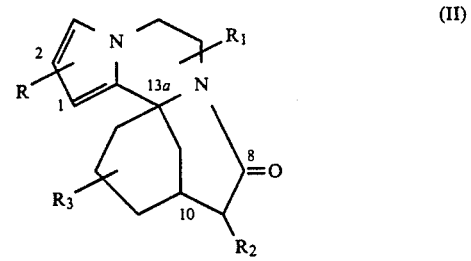

(II)

wherein R and $R_1$–$R_3$ independently represent hydrogen or lower alkyl.

2. A compound according to claim 1 wherein R and $R_1$ to $R_3$ represent hydrogen.

3. A compound according to claim 1 of the formula

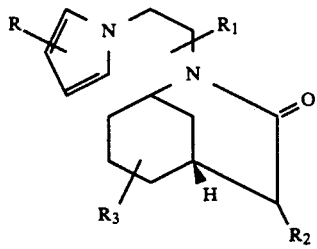

(III)

wherein R and $R_1$–$R_3$ independently represent hydrogen or lower alkyl.

4. A compound according to claim 3 wherein R and $R_1$ to $R_3$ represent hydrogen.

5. A pharmaceutical composition suitable for enhancing retention performance in conditions of amnesia in mammals comprising an effective retention performance enhancing amount of a compound according to claim 1 in combination with one or more pharmaceutically acceptable carriers.

6. A method of enhancing retention performance in conditions of amnesia in a mammal which comprises administering to a mammal in need thereof an effective retention performance enhancing amount of a compound of claim 1 in combination with one or more pharmaceutically acceptable carriers.

7. A method of enhancing retention performance in conditions of amnesia in a mammal which comprises administering to a mammal in need thereof an effective retention performance enhancing amount of a compound of claim 2 in combination with one or more pharmaceutically acceptable carriers.

* * * * *